(12) United States Patent
Holloway

(10) Patent No.: US 9,079,030 B2
(45) Date of Patent: Jul. 14, 2015

(54) SYSTEMS AND METHODS FOR BALANCING AND MAINTAINING THE HEALTH OF THE HUMAN AUTONOMIC NERVOUS SYSTEM

(76) Inventor: G. Blake Holloway, Kerrville, TX (US)

(*) Notice: Subject to any disclaimer, the term of this patent is extended or adjusted under 35 U.S.C. 154(b) by 327 days.

(21) Appl. No.: 13/162,446

(22) Filed: Jun. 16, 2011

(65) Prior Publication Data
US 2012/0149973 A1 Jun. 14, 2012

Related U.S. Application Data

(63) Continuation-in-part of application No. 11/021,405, filed on Dec. 22, 2004, now abandoned.

(51) Int. Cl.
*A61K 31/197* (2006.01)
*A61N 1/36* (2006.01)

(52) U.S. Cl.
CPC .......... *A61N 1/36025* (2013.01); *A61K 31/197* (2013.01); *A61C 2203/00* (2013.01); *A61N 1/36021* (2013.01)

(58) Field of Classification Search
CPC ............. A61K 31/197; A61C 2203/00; A61N 1/36021; A61N 1/36025
See application file for complete search history.

(56) References Cited

U.S. PATENT DOCUMENTS

| | | | |
|---|---|---|---|
| 4,190,654 A * | 2/1980 | Gherardi et al. | 514/221 |
| 5,084,007 A | 1/1992 | Malin et al. | |
| 7,346,395 B2 | 3/2008 | Lozano et al. | |
| 2006/0136009 A1 | 6/2006 | Staffel et al. | |
| 2007/0203432 A1 | 8/2007 | McNew | |

FOREIGN PATENT DOCUMENTS

WO 2006071268 A1 7/2006

OTHER PUBLICATIONS

Lapin, 2001, CNS Drug Reviews, vol. 7, No. 4, pp. 471-481.*
Smith et al., "Fear of Dental Care, Are We Making Any Progress?," JADA, 2003-08, pp. 1101-1108, v. 134, American Dental Association, U.S.
Scouarnec et al., "Use of Binaural Beat Tapes for Treatment of Anxiety: A Pilot Study of Tape Preference and Outcomes," Alternative Therapies, 2001-01, pp. 58-63. v. 7-1, InnoVision Communications, Aliso Viejo, CA, U.S.
Hinterberger et al., "Brain Areas Activated in fMRI during Self-Regulation of Slow Cortical Potentials (SCPs)," Exp. Brain Res. (resources.metapress.com), Jun. 27, 2003, pp. 113-122, v. 152, Springer-Verlag, Tübingen, Germany.
Gunkelman, "EEG Biofeedback as a Treatment for Substance Use Disorders: Review, Rating of Efficacy, and Recommendations for Further Research. Part 2," www.qeegsupport.com, Nov. 6, 2008, pp. 1-6.
Peniston, "The Peniston-Kulkosky Brainwave Neurofeedback Therapeutic Protocol: the Future Psychotherapy for Alcoholism/PTSD/Behavioral Medicine," www.aaets.org, pp. 1-5, American Academy of Experts in Traumatic Stress, U.S.

* cited by examiner

*Primary Examiner* — Kara R McMillian
(74) *Attorney, Agent, or Firm* — Kammer Browning PLLC

(57) ABSTRACT

A protocol or procedure is provided for lowering sympathetic nervous system arousal in a person in order to prepare that person for a medical or dental procedure. First, a therapeutic dosage of one or more neurotransmitter supplements, such as a gamma aminobutyric acid formulation, a tryptophan-derived neurotransmitter precursor, and dehydroepiandrosterone are administered to the patient. Concomitantly, gelled electrodes are placed adjacent or below the mastoid. The gelled electrodes are connected to a cranial electrotherapy stimulation device that administers a sub-sensation level current to the patient. Also, a noise dampening headset is placed on the patient and a neuroacoustic entrainment recording or program is played. Next, light is blocked with black out glasses. Then, the medical or dental procedure is performed.

13 Claims, 16 Drawing Sheets

| Physiologic Marker | Sympathetic Stimulation Response | Parasympathetic Stimulation Response | Full Protocol Results |
|---|---|---|---|
| HR | ↑ | ↓ | |
| SDNN | | | ↑ |
| RMSSD | | | ↑ |
| HRV Amp | ↓ | ↑ | ↑ |
| %HF | ↓ | ↑ | ↑ |
| %LF | ↑ | ↓ | ↑ |
| LF/HF | ↑ | ↓ | ↓ |
| SCP | | | ↓ |
| β Amp | ↑ | ↓ | ↓ |
| δ Amp | | | ↓ |
| % α over θ | ↓ | ↑ | ↑ |
| GSR | ↑ | ↓ | ↓ |
| BVP Amp | | | |
| Temperature | ↓ | ↑ | ↑ |

Fig. 3

(Results)

(GSR)

(BVP Amp)

(Temp)

(Temp)

(HRV Amp)

(%HF)

(%LF)

(SDNN)

(RMSSD)

(SCP)

(β Amp)

(δ Amp)

(% α ^ θ)

SYSTEMS AND METHODS FOR BALANCING AND MAINTAINING THE HEALTH OF THE HUMAN AUTONOMIC NERVOUS SYSTEM

CROSS REFERENCE TO RELATED APPLICATIONS

This application is a Continuation-in-Part of U.S. patent application Ser. No. 11/021,405; Filing Date: Dec. 22, 2004, the full disclosure of which is incorporated herein by reference.

BACKGROUND OF THE INVENTION

1. Field of the Invention

This invention relates to medical and dental care, and more particularly to an anxiety reduction protocol designed to lower sympathetic nervous system arousal in a person.

2. Description of the Related Art

Individuals who have unwarranted and inappropriate fears and anxiety about medical and dental treatments often refuse needed medical and dental care. Even when such individuals agree to undergo a medical or dental procedure, their fears and anxiety can make the experience unnecessarily unpleasant, leading to a suboptimal healthcare outcome. There is therefore a need for a method of providing individuals relief and remediation from anxiety and phobia in preparation for a medical or dental procedure.

SUMMARY OF THE INVENTION

A protocol or procedure is provided for rapidly lowering sympathetic nervous system arousal in a person in order to prepare that person for a medical or dental procedure and allows for a rapid recovery to pre induction state. First, a therapeutic dosage of one or more neurotransmitter precursors and analogs supplements, such as a gamma aminobutyric acid analog, a phenabut analog, a tryptophan-derived neurotransmitter precursor, casein trypic hydrolysate neurotransmitter precursor and dehydroepiandrosterone (DHEA) are orally or sublingually administered to the patient. Concomitantly, gelled electrodes are placed adjacent or below the mastoid. The gelled electrodes are connected to a cranial electrotherapy stimulation device that administers a sub-sensation level current to the patient. Also, a noise dampening headset is placed on the patient and a neuroacoustic entrainment software recording or program is played. Next, light is blocked out with out black out glasses. Then, the medical or dental procedure is performed.

BRIEF DESCRIPTION OF THE DRAWINGS

FIG. 3 is a chart showing the physiologic markers evidencing the efficacy of the protocol of the present invention and marker characteristics under sympathetic and parasympathetic stimulation.

DETAILED DESCRIPTION

Although the following specific details describe aspects of various embodiments of the invention, persons reasonably skilled in the art will recognize that various changes may be made in the details of the invention without departing from its spirit and scope as defined in the appended claims. Therefore, it should be understood that, unless otherwise specified, this invention is not to be limited to the specific details shown and described herein.

Figure 1:
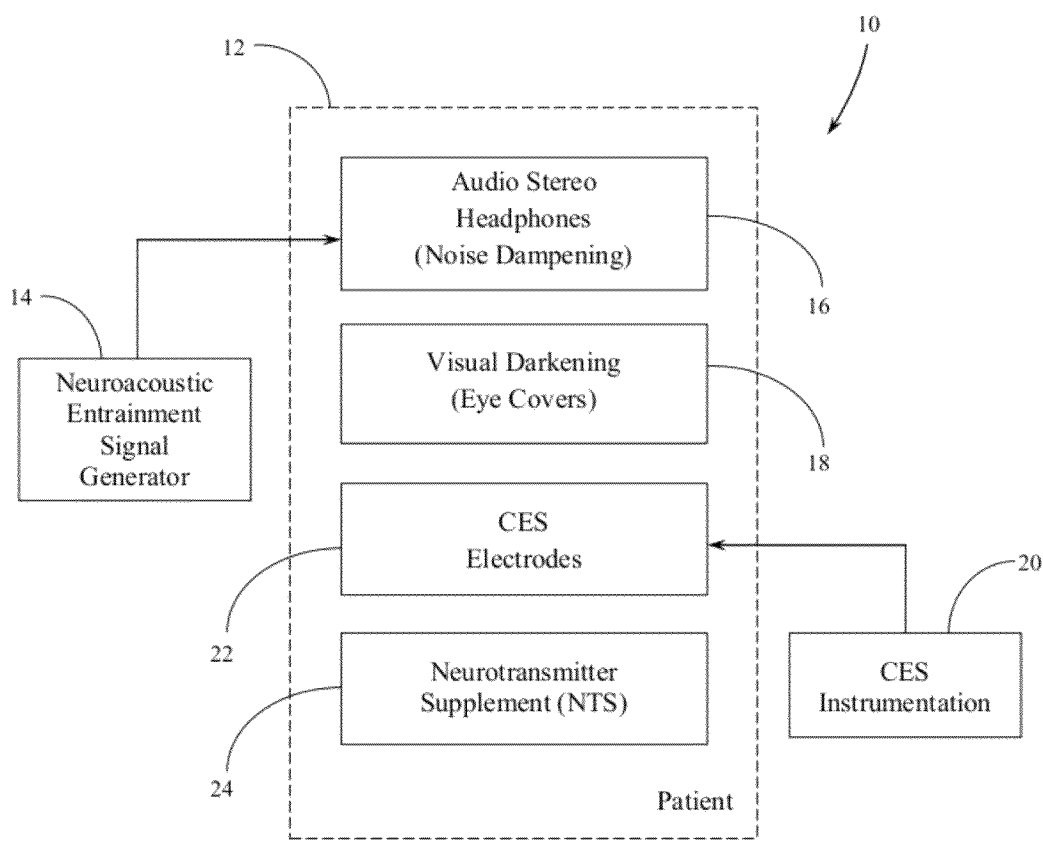
FIG. 1 is a schematic block diagram illustrating the essential components in the system for implementing the protocol of the present invention.

FIG. 1 is a diagram illustrating the components of the protocol 10 of the present invention. In FIG. 1, patient 12 receives noise dampening audio stereo headphones 16, visual darkening eye covers 18, cranial electrical stimulator electrodes 22, and a neurotransmitter supplement 24. A neuroacoustic entrainment signal generator 14 is attached to the patient 12 via the headphones 16. Cranial electrical stimulator instrumentation 20 is attached to the patient 12 via the CES electrodes 22.

Figure 2:
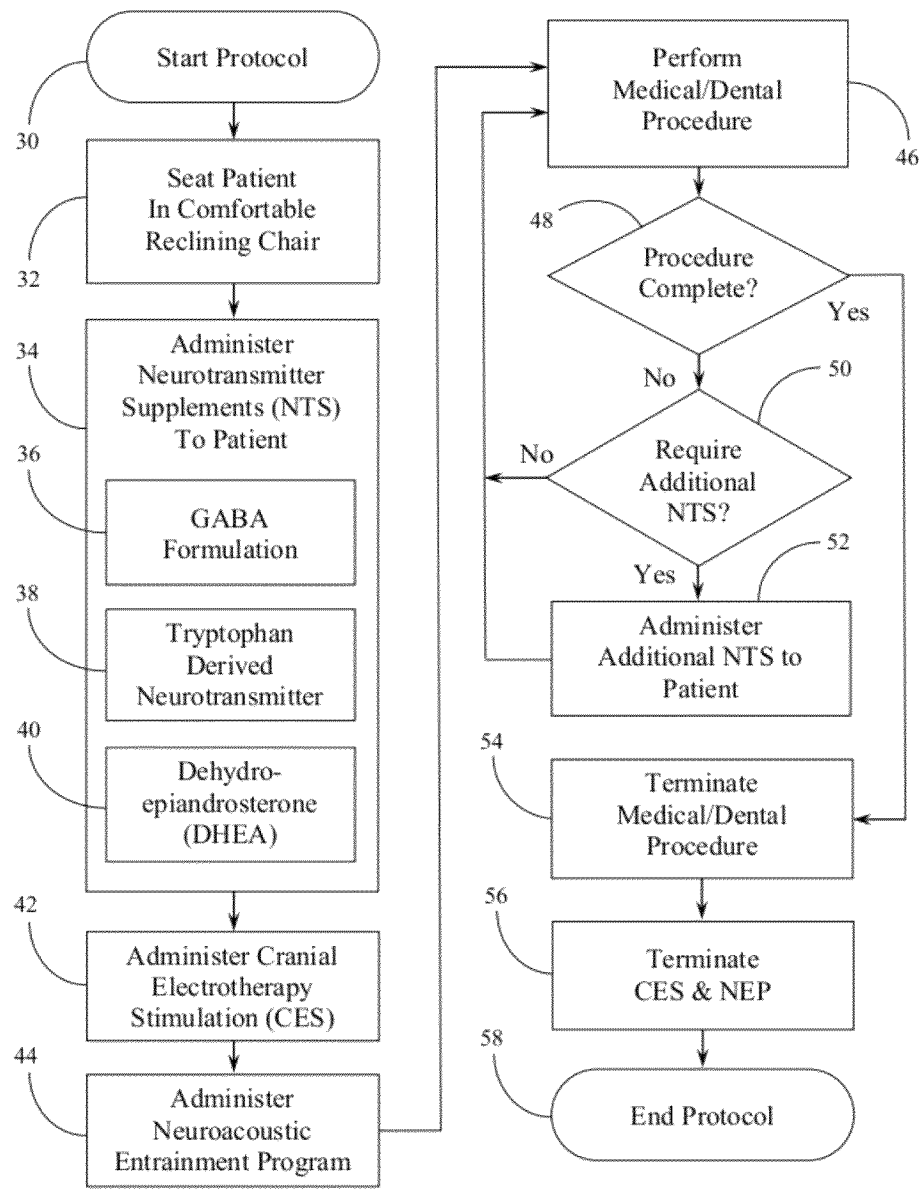
FIG. 2 is a flow chart illustrating the method steps associated with the process of administrating the protocol of the present invention.

FIG. 2 is a flow chart of one embodiment of the steps of the protocol of the present invention for preparation of a patient for a medical or dental procedure. This method rapidly lowers sympathetic nervous system arousal in a person in order to prepare that person for a medical or dental procedure. The patient should arrive at the clinic up to forty minutes prior depending upon the planned procedure. When ready to start the protocol 30, the patient is seated in a comfortable reclining chair 32. A therapeutic dosage of one or more neurotransmitter analogs/precursor supplements is administered to the patient 34. For example, gamma aminobutyric acid analog formulations (both GABAa and GABAb agonists) 36, a tryptophan-derived neurotransmitter 38, and dehydroepiandrosterone 40 are sublingually administered to the patient. In an alternate embodiment, the neurotransmitter analogs/precursor supplements may be administered in the form of a cream which is applied transdermally, preferably to the area of the neck over the carotid arteries and to the area in each ear over Arnold's branch (auricular branch) of the vagus nerve. In step 42, concomitantly, gelled electrodes 22 are placed adjacent or below the mastoid. The gelled electrodes 22 are connected to a cranial electrotherapy stimulation (CES) device 20 that administers a sub-sensation level current to the patient. An optional timer causes the CES device 20 to administer the current to the patient on a continuous or intermittent basis. A noise dampening headset 16 is placed on the patient and a neuroacoustic entrainment recording or program is played 44. In step 46, the medical or dental procedure is performed.

In one embodiment, the cranial electrotherapy stimulation, neuroacoustic entrainment program, and neurotransmitter analogs/precursor supplementation regimens are administered only before, but not during, the dental or medical procedure. In another embodiment, one or more of the cranial electrotherapy stimulation, neuroacoustic entrainment software program, and neurotransmitter analogs/precursor supplementation regimens continue to be applied during the dental or medical procedure, particularly if the procedure is lengthy. As shown in FIG. 2, additional neurotransmitter analogs/precursor supplements may be given 52 to the patient if required. When the procedure is terminated 54, the cranial electrical stimulation and neuroacoustic entrainment program are terminated 56 and the protocol ends 58.

The present invention discloses that the concomitant administration of neurotransmitter analogs/precursor supplements, cranial electrotherapy stimulation, and neuroacoustic entrainment software have synergistic complementary effects on the stimulation of neurotransmitters (i.e., chemical substances that transmit nerve impulses across a synapse) associated with relaxation and a sense of well-being. The following paragraphs describe the importance, purposes, and benefits of administering these complementary regimens to patients about to undergo a medical or dental procedure.

The Neurobiology of Stress and Arousal

Several systems of the human body participate in responses to stress, including the sensory thalamus, the sensory cortex, the hippocampus, the amygdala, the hypothalamic-pituitary-adrenal axis (HPA axis), and the Autonomic Nervous System (ANS is made up of both the Sympathetic Nervous System (SNS) and the Parasympathetic Nervous System (PNS). In response to sensory stimulus that could indicate a danger, the sensory thalamus communicates with the amygdala through two pathways. The thalamus communicates directly and immediately through a sub-cortical pathway to the amygdala, without any intervening cognition. The thalamus also communicates indirectly and more slowly with the amygdala through the cortex and hippocampus. The cortex, which is involved with cognition, and the hippocampus, which stores conscious memories and provides contextual information, tells the amygdala whether a perceived threat is real.

The amygdala stores implicit memories such as conditioned responses to aversive stimuli and emotional memories associated with fear. It comprises several physically close but functionally distinct nuclei. The basolateral complex of the amygdala processes inputs from the sensory system and perceives and evaluates the significance of a threat posed by that sensory system input. Its main output is the central nucleus of the amygdala, which is involved in emotional arousal. The central nucleus, in turn, sends fear-signaling impulses to the hypothalamus.

In response to fear-signaling impulses, the hypothalamus releases a stress hormone called corticotrophin-releasing factor (CRF), which in turn stimulates the pituitary gland to release the stress hormone adrenocorticotropic hormone (ACTH), which in turn stimulates the adrenal cortex to release coricosteroids into the blood stream. Corticosteroids, such as cortisol, are important to developing the body's fight or flight response to danger.

In response to fear-signaling impulses, the hypothalamus also activates the sympathetic nervous system (SNS). High SNS arousal is responsible for the uncomfortable symptoms of anxiety. The SNS prepares the body for immediate and vigorous defensive action by tightening muscles, constricting blood vessels, increasing the heart rate, metabolism, and blood pressure and sugar levels, dilating the eye's pupils and the lungs' trachea and bronchi, shunting blood to the skeletal muscles, liver, brain, and heart, stimulating the adrenal glands, and stimulating the liver to convert glycogen to glucose. The parasympathetic nervous system (PNS), by contrast, slows the heartbeat, constricts the bronchi, and generally restores the body to a normal state.

Both the SNS and PNS operate through neurotransmitters that communicate along the neural pathways of the SNS and PNS. The SNS and PNS each comprise (1) preganglionic neurons that connect the central nervous system (CNS) to ganglions of the body; and (2) postganglionic neurons that run from the ganglions to the effector organ.

Preganglionic sympathetic neurons release the excitatory neurotransmitter acetylchloline, and postganglionic sympathetic neurons release noradrenaline (also called norepinephrine). Because each preganglionic sympathetic neuron usually synapses with many postganglionic neurons, and because some of the neurons release noradrenaline and adrenaline (also called epinephrine) directly into the blood, activation of the SNS generally affects several body functions simultaneously.

As noted above, the neural systems of the body that participate in the physiology of stress and anxiety use neurotransmitters to communicate. Two of the most prominent inhibitory neurotransmitters are gamma aminobutyric acid (GABA) and serotonin. GABA is the primary inhibitory neurotransmitter of the central nervous system. GABA receptors are found on 25-40% of the synapses of the brain. When GABA binds to a GABA receptor, it opens a chloride channel allowing negatively charged chlorine ions into the interior of the nerve cell. This, in turn, polarizes the neuron which inhibits further presynaptic release of neurotransmitters. By inhibiting neural firing, GABA suppresses anxiety-related messages from reaching the cortex.

When subjected to prolonged stress or anxiety, the brain depletes its available store of GABA and other inhibitory neurotransmitters. This can culminate in a full-blown anxiety or panic attack, accompanied by excessive sweating, trembling, muscle tension, weakness, disorientation, breathing difficulty, fear, and other symptoms.

Serotonin is a neurotransmitter produced by neurons located in the locus coeruleus and raphe nuclei of the brain. The locus coeruleus and raphe nuclei innervate the thalamus, cerebral cortex, and hippocampus. Low levels of serotonin are associated with depression, anxiety, sleeplessness, impulsive behavior, aggression, and violent activity.

Neurotransmitter Supplementation

The use of a therapeutic dosage of neurotransmitter precursor supplement in preferred embodiments of the present invention has an anxiolytic effect on the brain by relieving anxiety and reducing tension on the patient.

In one embodiment, the patient is administered a therapeutic dosage of an amino acid formula comprising: 1-6 mg of magnesium (in the form of magnesium taurinate), 50-200 mg of GABA and PhenylGABA, 10-80 mg of glycine, 10-40 mg of N-Acetyl-L-Tyrosine, and 5-20 mg of taurine (also in the form of magnesium taurinate). This formula contains three of the main inhibitory neurotransmitters plus N-Acetyl L-Tyrosine, which is a precursor of norepinipherine, another neurotransmitter. Together, the formula has an inhibitory effect on the neurons of the brain, and therefore reduces sympathetic nervous system arousal. The formula is preferably administered in the form of one or more chewable or sublingual tablets or sublingual lipotropic sprays. By administering the formula sublingually, the formula is absorbed directly into the bloodstream through the blood vessels under the tongue and in the cheeks, allowing quick entry of the formula into the system and passing the blood brain barrier.

In a second embodiment, the patient is administered a neurotransmitter supplementation formula comprising a combination of vitamin B6, vitamin C, bioflavonoids, and tryptophan or L-5-hydroxytryptophan (L-5-HTP) and casein tryptic hydrolysate (CTH). A therapeutic dosage of one such combination comprises 25-400 mg of L-Theanine, 10-150 mg of L 5 Hydroxy-Tryptophan, 20-100 mg of Pyridoxal-5'-phosphate (i.e., vitamin B6), and 100-800 mg of ascorbic acid (i.e., vitamin C) and 5-500 mg CTH. The patient's own response to the regimen may dictate the actual dosage rate. Like the amino acid formula described above, the serotonin-boosting formula is preferably administered sublingually, through one or more tablets or lipotropic sprays. Alternatively, it is administered in the form of an enterically-coated capsule meant to be swallowed. The enteric coating enables the capsules to bypass enzymes in the stomach that would convert the L-5-HTP to serotonin prematurely, before reaching the central nervous system.

Tryptophan-derived neurotransmitter precursors serve as the precursor for the synthesis of serotonin (i.e., 5-hydroxytryptophan or 5-HTP) and melatonin (N-acetyl-5-methoxytryptamine). Vitamin B6 is the co-factor for enzymes that convert 5-hydroxy-tryptophan to serotonin, and Vitamin C catalyzes the hydroxylation of tryptophan to serotonin.

In a third embodiment, the patient is administered dehydroepiandrosterone (DHEA). DHEA, a hormone naturally secreted by the adrenal gland, is a signaler that reduces the level of the stress hormone cortisol in the body. This addition to the formulary provides some systemic relief for individuals under chronic stress and/or anxiety.

Preferred embodiments administer a combination of some or all of the foregoing supplements.

Neuroacoustic Entrainment

The incorporation of neuroacoustic entrainment software into preferred embodiments of the present invention is intended to evoke certain brainwave frequencies that are involved in producing relaxation, dissociation and the first stage of sleep.

The electrochemical activity of the brain produces measurable electromagnetic wave forms. Electroencephalographs (EEGs) of the brain can quantify this activity in terms of amplitude and frequency. Research has associated different brainwave frequencies with different mental states. At frequencies of between 13 and 40 Hz (i.e., Beta brainwaves), the mind is active, alert and able to focus on details. Beta brainwave states are associated with conversation and competitive physical activities. Between 8 and 13 Hz (i.e., Alpha brainwave states), the mind is more relaxed and reflective. Alpha brainwave states are associated with creativity, contemplation, and visualization. Theta brainwave states, which operate in the range of 4 to 8 Hz, are associated with dreaming, intense creativity, visualization ability, meditation, and out-of-body experiences. The brain cells reset their sodium and potassium ratios in the Theta state, which helps explain why sleep is important to healthy mental function. Delta brainwave states, which operate in the range of 0.5 to 4 Hz, are associated with unconsciousness, very deep and dreamless sleep, and long term memories. Some very experienced and disciplined meditative individuals are able to train their minds to operate in the Delta state while conscious.

A normal healthy human brain cycles through each of these brainwave states throughout the day and night. And because not all parts of the brain are equally active at all times, the brain typically operates in several brainwave states at the same time. A person's state of mind or level of consciousness is typically associated with the dominant brainwave state.

It is also believed that some brainwave frequencies promote the production and transmission of certain neurotransmitters more than other brainwave frequencies. One study associated a 10 Hz brainwave pattern with enhanced production and turnover of serotonin. For this reason, it is believed that by entraining the brain to a given frequency, the production of some neurotransmitters can be enhanced.

There are various methods of entraining brainwave states, including disciplined meditation, chanting, and hypnosis. Most methods evoke a response for the brain to operate in a given brainwave state by subjecting it to a repeated stimulus, such as pulses of sound, volume modulation, monaural beats, binaural beats, or pulses of light. A constant, repeated 10 Hz stimulus applied to the brain can stimulate a 10 Hz brainwave state. This phenomenon is called the "frequency following response."

In the preferred embodiments of the present invention, a noise dampening headset is placed over the patient's ears and connected to a neuroacoustic entrainment recording (digital software file in the preferred embodiment). In one embodiment, the recording preferably includes a sound or melody that is volume modulated at frequencies designed to evoke higher levels of alpha or theta brainwaves and reduce beta brainwaves.

In another embodiment, the recording is designed to make the brain perceive one or more binaural beats. Binaural beats occur when signals of two different frequencies are presented separately, one to each ear. Each ear is hardwired to an olivary nucleus (a sound processing center of the brain) in the corresponding hemisphere of the brain. The brain, in trying to reconcile the different noises it hears from each ear, perceives a "binaural beat." If a frequency of 100 Hz is presented to one ear, and a frequency of 105 Hz is presented to the other, the brain will perceive a binaural beat of 5 Hz, and may ultimately be entrained to resonate at the binaural beat frequency.

In preferred embodiments of the invention, the neuroacoustic entrainment software uses a recording that introduces multiple binaural frequencies, preferably in the form of harmonically layered and patterned binaural frequencies. In this manner, multiple frequency following responses are triggered in the brain at the same time. Furthermore, the neuroacoustic entrainment software's binaural frequencies are preferably blended together with instrumental music, soothing sounds of rain, or nature sounds.

Cranial Electrotherapy Stimulation

The incorporation of cranial electrotherapy stimulation (CES) into preferred embodiments of the present invention is intended to stimulate a balance in the nervous system's release and transmission of excitatory and inhibitory classes of neurotransmitters. CES, also known as microcurrent electrical stimulation or transcranial microcurrent stimulation, is the application of low-level, pulsed electrical currents to the head. The current is preferably delivered to the patient via conductive gel electrodes on or below the mastoid.

The current is preferably provided in the form of sinusoidal, rectangular, or modified rectangular wave pulses. The frequency is set between 0.1 and 1,000 Hz, optionally superimposed on a carrier wave of up to 150 kHz. The waveform is preferably biphasic and bipolar and has a 20-50% duty cycle. The intensity of the current is set at a stable level below the sensation threshold (e.g., between 0.01 mA and 7 mA, more preferably about 0.1 mA). The CES device 240 should be able to adjust the voltage for varying levels of resistance in order to provide a stable level of current. CES is preferably applied for at least 30 minutes, and as long as 6 hours. The frequency pattern and current level may be adjusted from time to time to prevent physiological accommodation.

CES is thought to stimulate the vagus nerve, and thereby promote PNS dominance. CES also focuses current on the hypothalamic region of the brain, where it influences both the pre-synaptic release and post-synaptic reception of neurotransmitters. The current increases brain cell membrane permeability by low level electrophoresis that improves neurotransmitter absorption. The current increases serotonin and endorphin levels in the brain and decreases the level of the stress hormone cortisol in the brain. It also promotes alpha brainwave states. It is believed to operate by stimulating the neurons of the brain to accelerate their manufacture and reception of both inhibitory and excitatory neurotransmitters at the same rate, so that they mutually inhibit each other's further production, restoring the neurotransmitters to pre-stress homeostasis. For example, CES applied to an anxious patient will slow down the patient's norepinephrine neurons and speed up the patient's endorphin neurons, bringing them into homeostatic balance. For this reason, CES is believed to have a more dramatic effect on anxious patients, who are out of balance, than relaxed patients who are already in a homeostatic balance.

Synergistic Benefits

The concomitant use of neuroacoustic entrainment software, neurotransmitter precursor/analog supplementation, electro-stimulation, and light blocking glasses has many synergistic benefits. CES and neuroacoustic entrainment both rapidly promote homeostasis between the sympathetic and parasympathetic nervous systems, thereby lowering sympathetic system arousal. The use of CES together with neuroacoustic entrainment promotes relaxing alpha brainwave states more than might be achieved with neuoacoustic entrainment alone. The use of neurotransmitter supplements helps to prevent pre-synapse vesicle depletion that might otherwise occur with CES if sufficient precursor amino acids are not available. Furthermore, all three treatments increase the release of inhibitory neurotransmitters. The restoration of neurochemical homeostais remediates the excitatory neurological events that form the basis of severe anxiety. Upon discontinuing the protocol, there is a rapid recovery to the initial condition with no side effects.

A conformational single blind study was conducted to gather data to support the experience of anxious dental patients who have used the studied protocol to help them undergo procedures that, in the past, caused them severe anxiety requiring sedation. A small sample of subjects with evoked anxiety were exposed to Cranial Electrotherapy Stimulation, Neuroacoustic Software and administered Amino Acid Supplements composed of GABA, 5HTP, Theanine with cofactors in the full protocol. In this study, the subjects received all of the above components on a second day except the Non-Neuroacoustic Software (soothing music) was substituted for the Neuroacoustic Software, this was called the Sham treatment.

The research study was divided into two phases. Phase I included measurements of GSR. Data collected from subjects in phase II included GSR readings and EEG taken at "cz". All data were recorded using Thought Technologies BioGraph ProComp: Version 2.0. Channels Alpha, Theta, Beta and GSR were selected for analysis. The Anxiety Survey was a modified anxiety checklist, given post-evoked anxiety and then again post-treatment on both treatment days.

When comparing data subjects exposed to the full treatment showed, on average, a 30 point decrease in anxiety levels and a 4.47 microvolt decrease in the GSR recordings than sham treatment produced. The EEG data from the Neuroacoustic Software treatment as compared to the sham treatment showed an average decrease in the Beta brainwave power of −0.30 indicating a decrease in vigilance and an increase in relaxation. In addition, the Theta and Alpha brainwaves showed an increase in power, Theta +0.7 and Alpha +1.8. Both of these increases indicate the subject became more relaxed and restful. This is in comparison to the sham treatment that showed an increase in Beta (more vigilance), a −0.05 microvolt decrease in Theta (less restful) and a 1.34 microvolt difference in Alpha (less relaxed). As Theta and Alpha power increased subjects became more relaxed and therefore more likely to be less agitated during a medical and or dental procedure.

Along with the brainwave and GSR data it is essential to look at the subjects decrease in perceived anxiety as indicated by a reduction in their anxiety score and their reflections after each days study. Subjects reflected that with both protocols they felt more relaxed but on the day they received the full protocol their mind was able to let go of their thoughts and they become much more at ease and at peace than on the day they received the sham Neuroacoustic Software. They reported that they felt better able to manage their stress and anxiety causing situations after the full treatment than with the partial treatment. Neuroacoustic Software when used with CES and Supplements rapidly reduces anxiety and increases relaxation better than when CES and Supplements are used alone.

Human Physiological Homeostasis

The balance between the sympathetic and parasympathetic branches of the autonomic nervous system is essential to human physiological homeostasis. The autonomic nervous system receives input from parts of the central nervous system that process and integrate stimuli from the body and external environment. The actions of the parasympathetic nervous system can be summarized as rest and restoration. The vagus nerve contains about 75% of all parasympathetic fibers. The dominant sympathetic nervous system response is a driver for numerous negative physiological and psychological states. These metabolic consequences are well documented in the prior art. A functional level of sedation requires that the body be in a dominant parasympathetic state.

Physiological Markers

Numerous physiological markers are available which provide data to analyze the efficacy of the clinical system of the present invention in decreasing the sympathetic nervous system response and anxiety. These markers include: galvanic skin response, temperature, blood volume pulse, heart rate, heart rate variability (including HRV amp, SDNN, RMSSD, % LF, % HF, and LF/HF) and brain waves (including alpha, theta, beta, and delta amplitudes, alpha theta crossover and slow cortical potentials). As shown in FIG. 3, each of these physiologic markers demonstrates a particular response (increase or decrease) under sympathetic and parasympathetic stimulation.

Galvanic skin response (GSR) is a method of measuring the electrical conductivity of the skin, which varies with its moisture level. This is notable because the ecrine glands are controlled by the sympathetic nervous system, so skin conductance is used as an indication of psychological or physiological arousal. There is a relationship between sympathetic activity and emotional arousal such as fear and anger. The GSR is highly sensitive to emotions in some people. Human ecrine glands receive primary signals from sympathetic cholinergic fibers that are controlled by the neurotransmitter acetylcholine. In measuring GSR, a very slight electrical current is run through the skin and changes in the salt and water in the sweat gland ducts are measured. The more emotionally aroused the subject is, the more active the sweat glands are and the greater the electrical conductivity of the skin. An increase in GSR occurs with sympathetic stimulation and decreases with parasympathetic stimulation.

Dermal temperature is another measure of sympathetic arousal. Dermal temperature decreases with sympathetic stimulation and increases with parasympathetic stimulation.

Blood volume pulse (BVP) is measured by a photoplethysmograph which is a non-invasive transducer to measure the relative changes of blood volume in a subject's finger or temple. An infrared light source is transmitted through or reflected off the tissue, detected by a phototransistor, and quantified in arbitrary units. Less light is absorbed when blood flow is greater, increasing the intensity of the light reaching the sensor. The wave form obtained from such a transducer represents the BVP of the subject, which is the phasic change in blood volume with each heartbeat. Heart rate is simply the number of beats of the heart per time interval. Heart rate increases with sympathetic stimulation and decrease with parasympathetic stimulation. The BVP likewise increases with sympathetic stimulation and decreases with parasympathetic stimulation.

Heart rate variability (HRV) consists of beat-to-beat differences in intervals between successive heartbeats. In general, emotional stress gives rise to heart rhythm patterns that appear irregular and erratic. The heart rate variability (HRV) waveform under stress appears as a series of uneven, jagged peaks, i.e., an incoherent heart rhythm pattern. Physiologically, this pattern indicates that the signals produced by the two branches of the autonomic nervous system are out of sync with each other. This incoherent pattern of physiological activity associated with stressful emotions can cause the body to operate inefficiently, deplete energy, and produce extra wear and tear on the body. This is especially true if emotional stress is prolonged or frequent. During positive emotions, the heart rhythm pattern becomes highly ordered, looking like a smooth, harmonious wave. This is called a coherent heart rhythm pattern. With coherent heart rhythm, the activity in the two branches of the autonomic nervous system is synchronized and the body's systems operate with increased efficiency and harmony.

HRV data can identify anxiety and stressful influences on the cardiovascular system. The interbeat interval is a portal through which parasympathetic and sympathetic influences may be observed. HRV is a measure of the variation of the beat-to-beat interval. Increased HRV has been shown to have positive clinical significance, whereas reduced HRV has been associated with negative clinical outcomes and conditions. Variation in the beat-to-beat interval is a physiological phenomenon resulting from several different inputs to the sinoatrial node, which is the impulse-generating, pacemaker tissue located in the right atrium of the heart, and thus the generator of normal sinus rhythm. The main inputs are the sympathetic and the parasympathetic nervous systems. The two primary fluctuations are respiratory arrhythmia and low-frequency oscillations. Respiratory arrhythmia is associated with the respiratory rate and low-frequency oscillations are associated with Mayer waves of blood pressure (waves in arterial blood pressure brought about by oscillations in baroreceptor and chemoreceptor reflex control systems).

The most widely used methods for measuring HRV are time-domain methods and frequency-domain methods. The time-domain methods are based on the beat-to-beat or NN intervals, which are analyzed in a variety of ways. Included among these are the SDNN (the standard deviation of NN intervals) and the RMSSD (the square root of the mean squared difference of successive NNs). These are measures representing sympathetic or parasympathetic influence. Increased scores of these measures represent greater parasympathetic influence. Norms for these measures are: RMSSD 27.2+/−12.3 and SDNN 136.5+/−33.4.

Measurements assessed with frequency-domain methods include LF, LF norm, HF, HF norm, and LF/HF ratio. HRV rhythms in the low frequency (LF) range (between 0.04 to 0.15 Hz) reflect mixed sympathetic and parasympathetic activity. Mental stress increases LF activity and is usually considered a marker of sympathetic modulation. The high frequency (HF) range (between 0.15 to 0.4 Hz) contains rhythms regulated by parasympathetic activity and corresponds to N-N variations caused by respiration. Deep, even breathing activates the parasympathetic nervous system and raises the amplitude of HF. Mental stress decreases HF activity. Vagal activity is the major contributor to the HF component.

With the LF/HF ratio, high numbers mean dominance of sympathetic activity while low numbers mean dominance of the parasympathetic activity. After deep and even breathing, an increase reflects changes in the parasympathetic regulation. HRV decreases with sympathetic stimulation and increases with parasympathetic stimulation. Consistent with this result, the HRV LF % and the LF/HF ratio increase with sympathetic stimulation and decrease with parasympathetic stimulation.

Various brain waves are associated with states of wakefulness and sleep, mental activity related to cognitive, sensory and motor activities, and emotions such as fear and anxiety. Beta brain waves are the most rapid brain waves and reflect normal waking consciousness. Beta amplitudes increase with sympathetic stimulation. There is a range of beta waves: low beta, relaxed but alert (13-15 Hz), mid beta (around 15-19 Hz), and high beta, anxious brain (associated with fear and anxiety) exhibiting brain wave frequencies between 23-38 Hz. Alpha waves indicate a comfortable, relaxed state, 8-13 Hz, and are associated with relaxation, meditation, and idleness. Theta waves reflect a deeply relaxed state, 4-8 Hz. Delta waves are indicative of the sleep state wherein signals are moving through clusters of neurons very slowly, around 4 Hz. Delta amplitude progressively decreases during sleep. Delta waves are related to V waves which occur during sleep and to slow cortical potentials (described below).

The production of alpha and theta patterns in the brain is correlated to the relaxation response. The relaxation response reduces heart rate and blood pressure, relaxes muscles, and increases oxygen to the brain. The fight or flight response is accompanied by beta brainwave frequencies (low-amplitude, high-frequency). The relaxation response reduces heart rate and blood pressure, relaxes muscles, and increases oxygen flow to the brain. The relaxation response is extremely beneficial to learning and problem solving and is accompanied by alpha (higher amplitude, lower frequency brainwaves) and theta rhythms (even greater amplitude, lower frequency brainwaves). The brain wave frequencies increase with sympathetic stimulation and decrease with parasympathetic stimulation.

Alpha to theta crossover occurs just at pre-sleep, providing a dissociative hypnogogic experience of profound relaxation. Alpha to theta crossover is at the heart of restorative sleep and the loss of a sense of time and place. It is called the healing zone or psychological dissociative state. The state of consciousness is similar to a meditative or hypnotic relaxed state. The alpha-theta crossover state is a deeply relaxed state in the alpha (8-12 hertz) and the theta (4-8 hertz) range, right on the edge of sleep. The name comes from the behavior of the brain waves. Alpha waves are usually higher in amplitude, or more powerful, than theta. When the amplitude of the alpha waves drops and the theta amplitude rises to the point where it crosses over the alpha waves, which means it has become more powerful, is called alpha-theta crossover. Alpha theta crossovers decrease with sympathetic stimulation and increase with parasympathetic stimulation.

Slow cortical potentials (SCPs) are gradual changes in the membrane potentials of cortical dendrites which are in the frequency range below 1-2 Hz that last from 300 ms to several seconds. Negative potential shifts indicate mobilization or higher excitability, positive SCP shifts represent reduced excitability or inhibition of neuronal activity. Slow cortical potential shifts in the electrical negative direction reflect the depolarization of large cortical cell assemblies, reducing their excitation threshold. SCPs increase with sympathetic stimulation and decrease with parasympathetic stimulation.

As can be seen in FIG. 3, each of these biophysiologic markers has an opposite response to sympathetic versus parasympathetic stimulation. For example, galvanic skin response increases with sympathetic stimulation and decreases with parasympathetic stimulation. Likewise, EEG beta amplitude, heart rate variability indicators LF/HF and HRV LF % increase with sympathetic stimulation and decrease with parasympathetic stimulation. Conversely, dermal temperature and heart rate variability amplitude decrease with sympathetic stimulation and increase with parasympathetic stimulation.

In the studies conducted to assess the effectiveness of the protocol of the present invention, data sets for each of these key biophysiological markers were collected pre-exposure, during, and post-exposure to both the full protocol and to the partial protocol. The present invention combines the effects of the various modalities to produce a statistically significant increase in parasympathetic tone (relaxation), hypnogogic and sleep states, and brain activation (decrease in SCP) in those individuals treated with the full protocol of the present invention as compared to the partial protocol. As shown in FIG. 3, the biophysiologic data confirmed that the full protocol of the present invention produced changes in the biophysiologic markers consistent with a sedative hypnogogic effect with parasympathetic dominance. In contrast, those subjects exposed to a partial protocol showed no significant change in the physiological markers. These results confirm the novel synergistic effects of the full protocol of the present invention and its efficacy in rapidly reducing anxiety as evidenced by reduction of sympathetic nervous system arousal.

In the current study, 30 random non-anxious volunteers of varying health states were tested first by exposure to the full protocol of the present invention and then to a partial protocol (after a minimum of 48 hours) to identify the synergistic benefits of the treatment combination of the present invention. In the study, the subjects receiving the partial protocol took the neurotransmitter precursor/analog supplement and received cranial electrotherapy stimulation set at 100 Hz. Those subjects receiving the full protocol of the present invention received the neurotransmitter precursor/analog supplement, cranial electrotherapy stimulation set at 0.5 Hz, black out glasses, and neuroacoustic entrainment software with music.

Key biophysiological signals were collected pre-exposure, during, and post-exposure for those subjects in both protocols. Data was collected from the full and partial protocols and compared to each baseline due to residual effects of the full protocol. The baseline data was compared for residual effects from the full protocol treatment. The objective was to assess internal changes and distinctive residual effects from the full protocol treatment. Efforts to show the reliability of the data as indicative of increased parasympathetic tone were made using available statistical analysis software.

As the attached Drawing figures demonstrate, data analysis with each of the physiologic markers was carried out by characterizing variances in the marker values from a baseline through a number of time differentiated segments during application of both the full and partial protocols. Analysis of these variances and comparisons between the full and partial protocol data sets show statistically relevant (non-random) trends in the data both within the specific time segments and across the duration of the testing.

Figure 4:
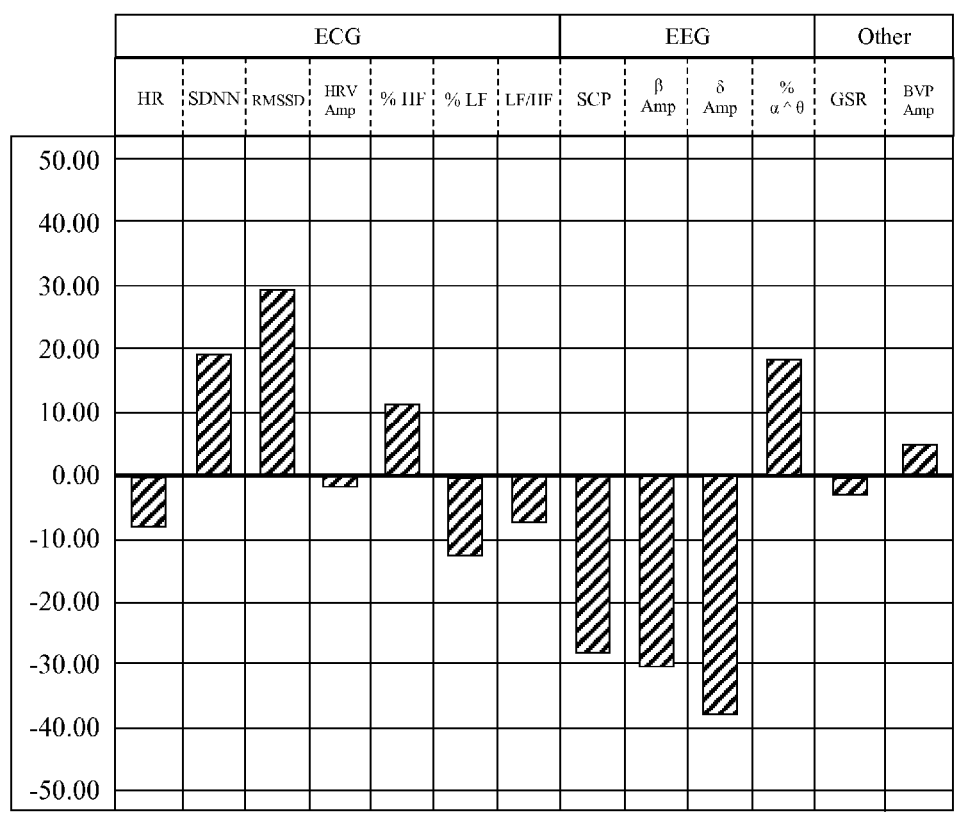
FIG. 4 is a bar graph illustrating statistically significant trends for the physiologic markers with application of the protocol of the present invention.
Figure 5:
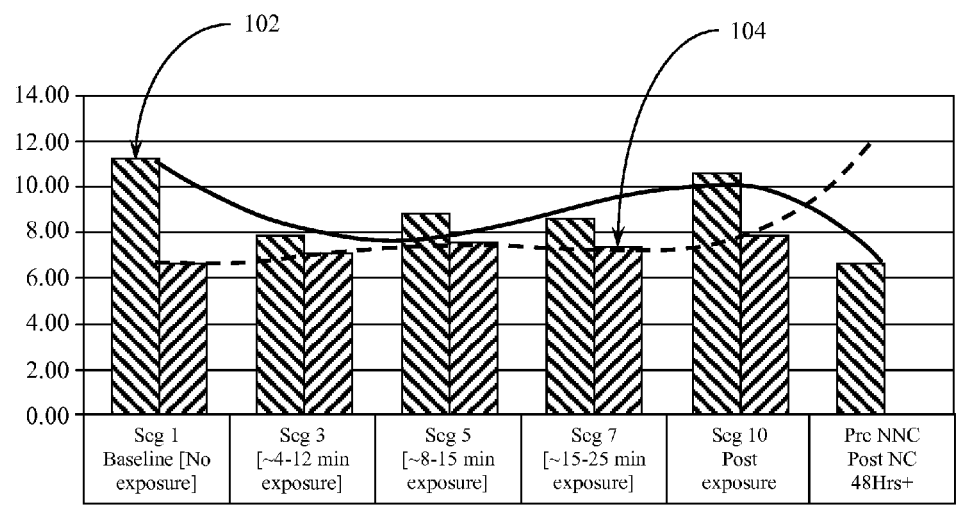
FIG. 5 is a bar graph illustrating full protocol and partial protocol GSR response.
Figure 6:
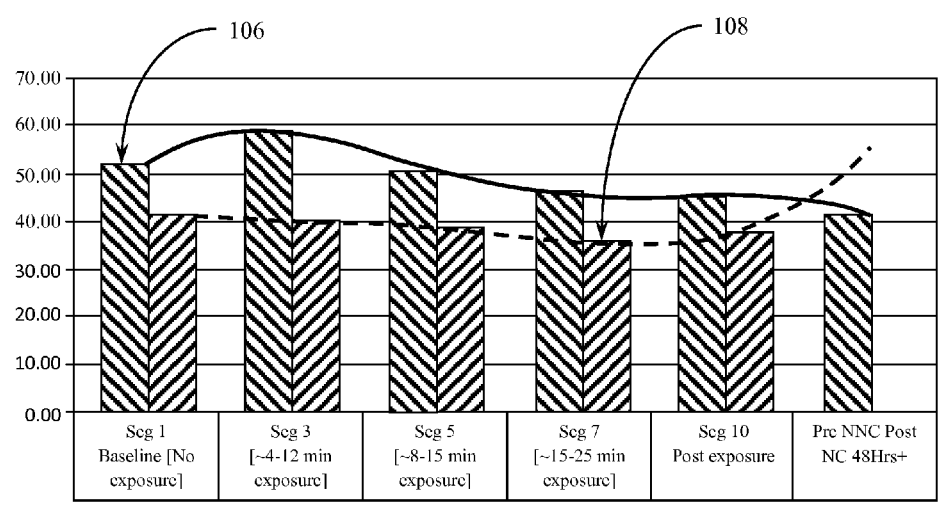
FIG. 6 is a bar graph illustrating full protocol and partial protocol BVP amplitude response.
Figure 7A:
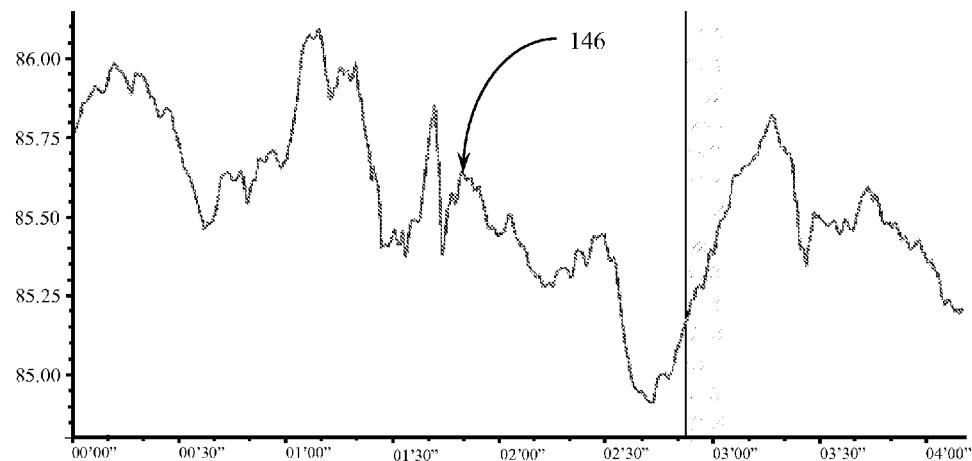
FIGS. 7A & 7B are graphs illustrating temperature variation for full protocol versus baseline.
Figure 7B:
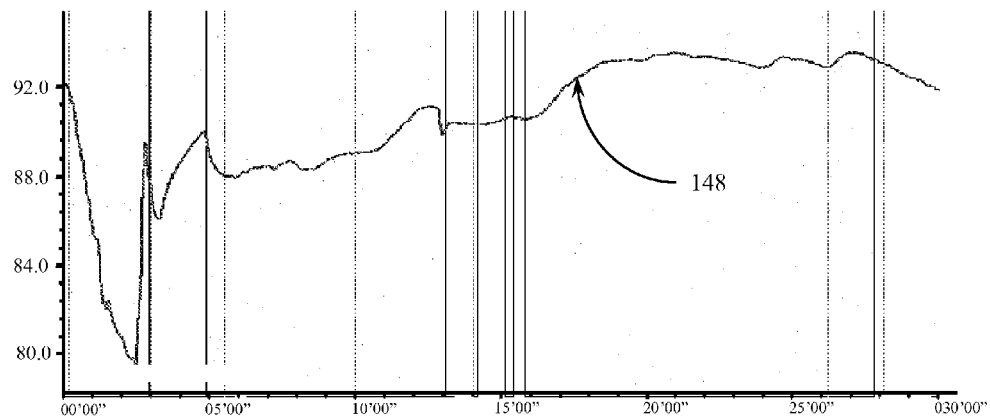

The subjects that received the full protocol of the present invention were in a more parasympathetic dominant state as evidenced by changes in biophysiologic markers as shown in FIG. 4. FIG. 4 shows the degree to which the full protocol has a statistically significant effect on the markers indicative of parasympathetic response. FIG. 5 shows the full protocol 102 and partial protocol 104 GSR response. The GSR response of the full protocol 102 exhibited downward trending with rapid induction, sustained effect, and rapid restoration to normal. FIG. 6 shows the full protocol 106 and partial protocol 108 BVP amplitude response. The BVP amplitude response of the full protocol 106 increased, with rapid induction and sustained effect. FIGS. 7A and 7B show temperature variation for baseline 146 versus full protocol 148. Dermal temperature response of the full protocol rose sharply, stabilized and maintained at an elevated temperature as compared to the baseline temperature.

Figure 8:
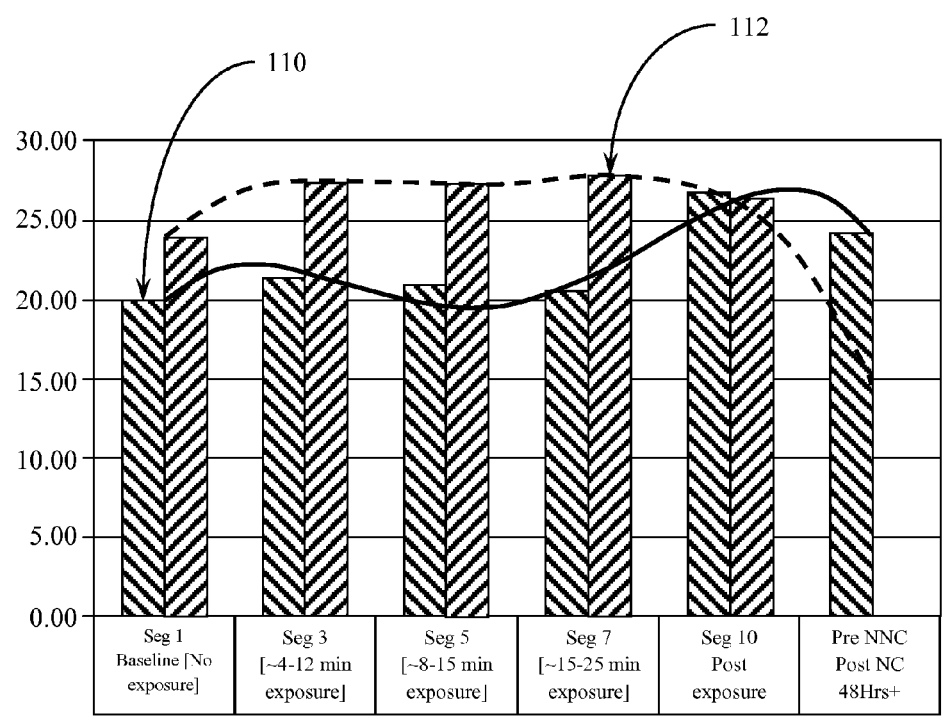
FIG. 8 is a bar graph illustrating full protocol and partial protocol HRV amplitude response.
Figure 9:
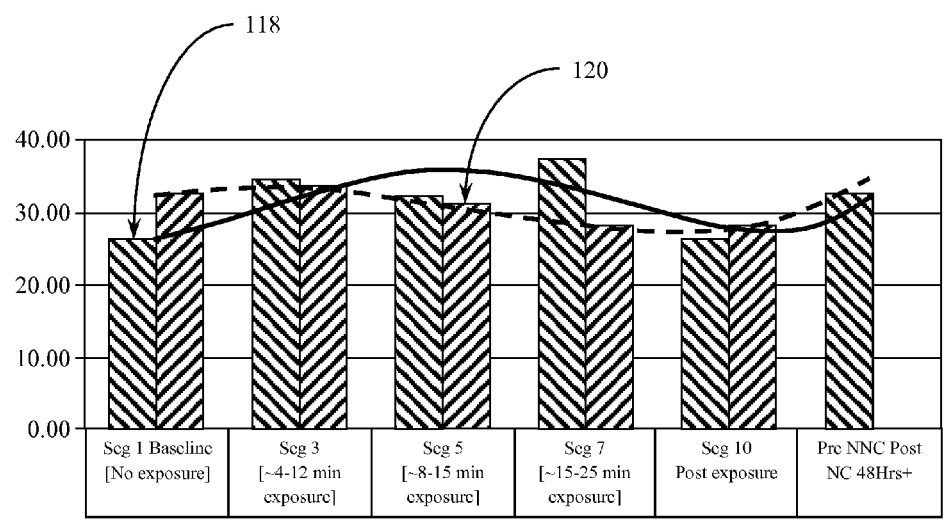
FIG. 9 is a bar graph illustrating full protocol and partial protocol % HF response.
Figure 10:
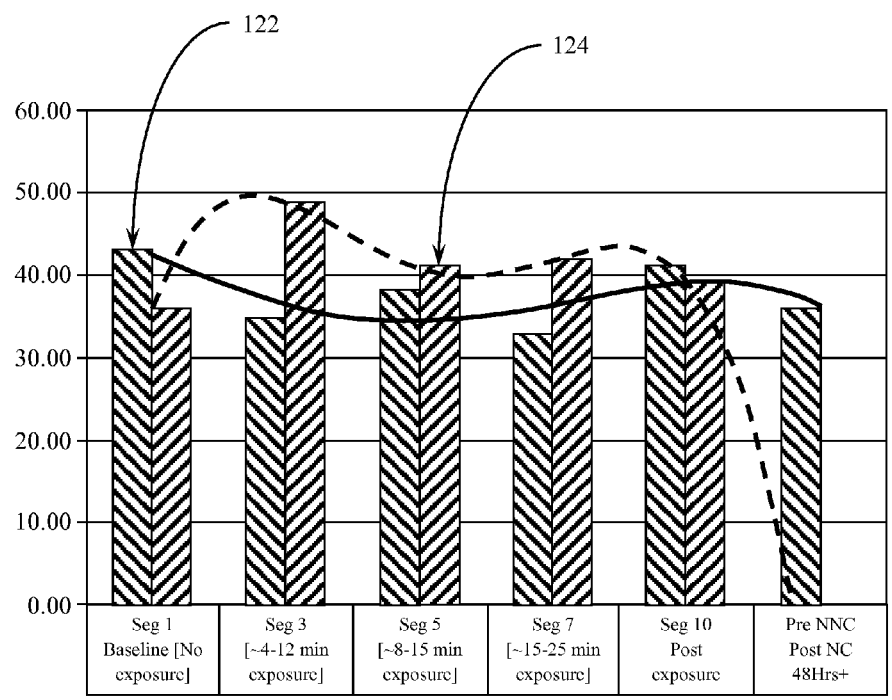
FIG. 10 is a bar graph illustrating full protocol and partial protocol % LF response.

FIG. 8 shows the full protocol 110 and partial protocol 112 HRV amplitude response. The HRV amplitude response of the full protocol increased, demonstrating a cumulative effect with a significant improvement from baseline post exposure that continues for more than 48 hours. FIG. 9 shows the full protocol 118 and partial protocol 120 % HF response. The % HF response of the full protocol showed parasympathetic dominance (increase) with return to normal. FIG. 10 shows the full protocol 122 and partial protocol 124 % LF response. The % LF response of the full protocol showed rapid reduction, sustained effect, and rapid restoration to normal.

Figure 11:
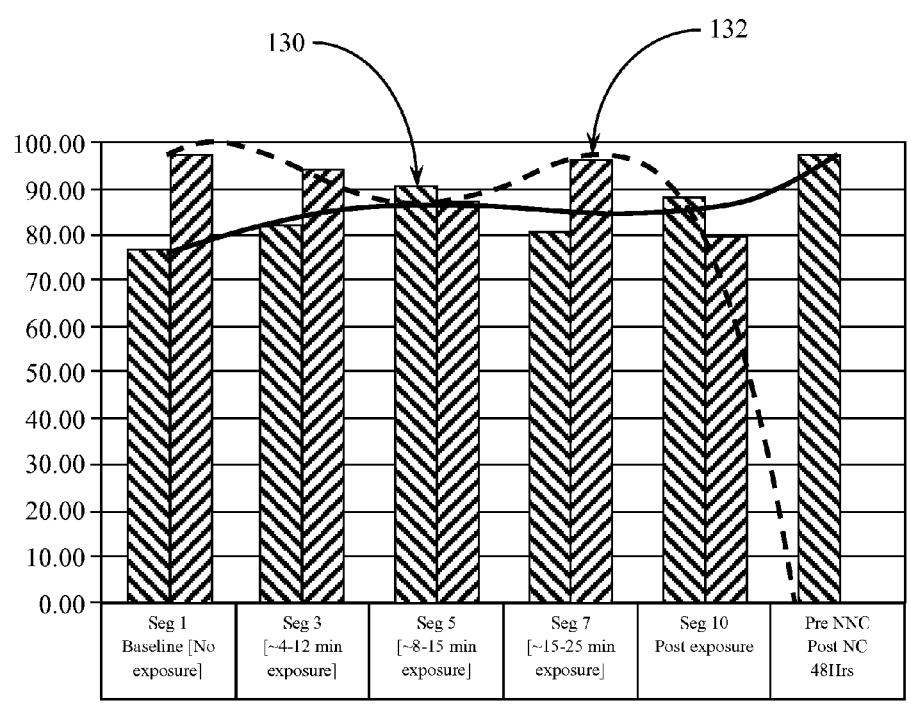
FIG. 11 is a bar graph illustrating full protocol and partial protocol SDNN response.
Figure 12:
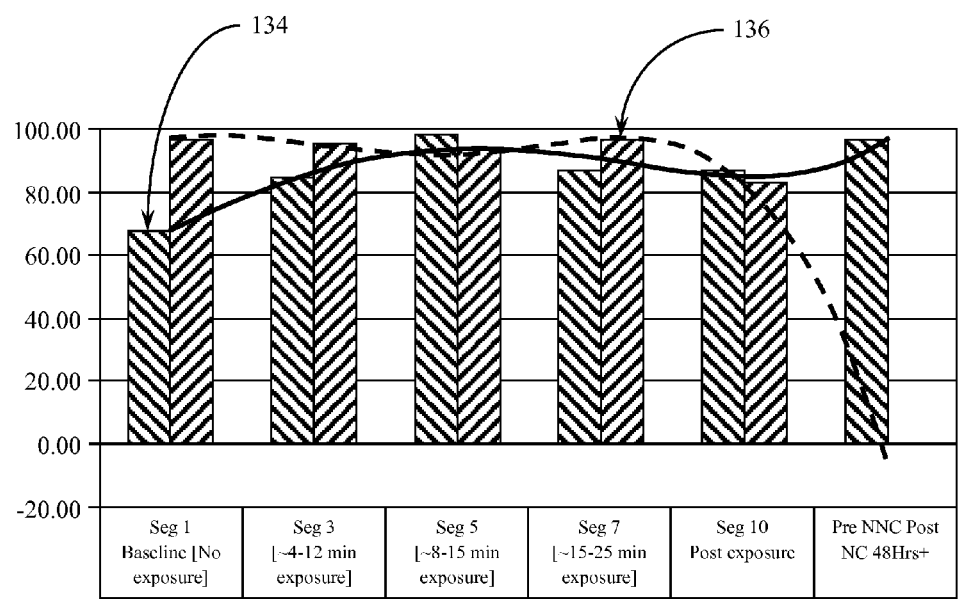
FIG. 12 is a bar graph illustrating full protocol and partial protocol RMSSD response.

FIG. 11 shows the full protocol 130 and partial protocol 132 SDNN response. The SDNN response of the full protocol showed a gradual increase in HRV during the protocol, sustained and increased over 48+ hours post exposure. Some subjects showed increases of 30-70% over a four week period. FIG. 12 shows the full protocol 134 and partial protocol 136 RMSSD response. The RMSSD response of the full protocol showed a gradual increase in HRV during the protocol, sustained and increased over 48+ hours post exposure. Some subjects showed increases of 30-70% over a four week period. The heart rate response of the full protocol decreased and the LF/HF ratio of the full protocol decreased. Overall, HRV analysis under the full protocol of the present invention demonstrated increased coherence of the cardiovascular state.

Figure 13:
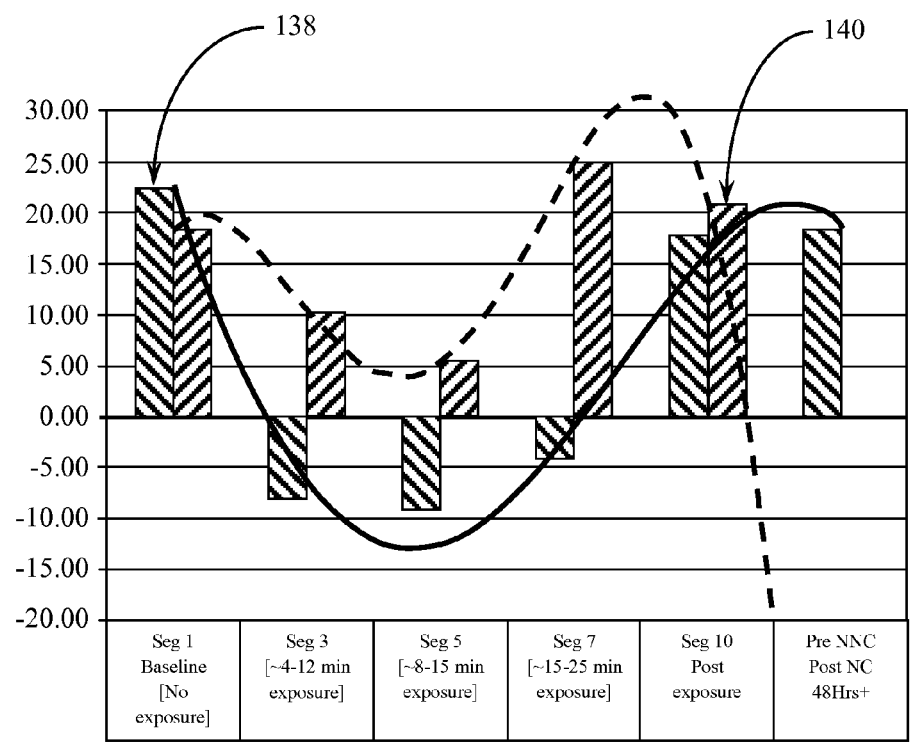
FIG. 13 is a bar graph illustrating full protocol and partial protocol SCP response.
Figure 14:
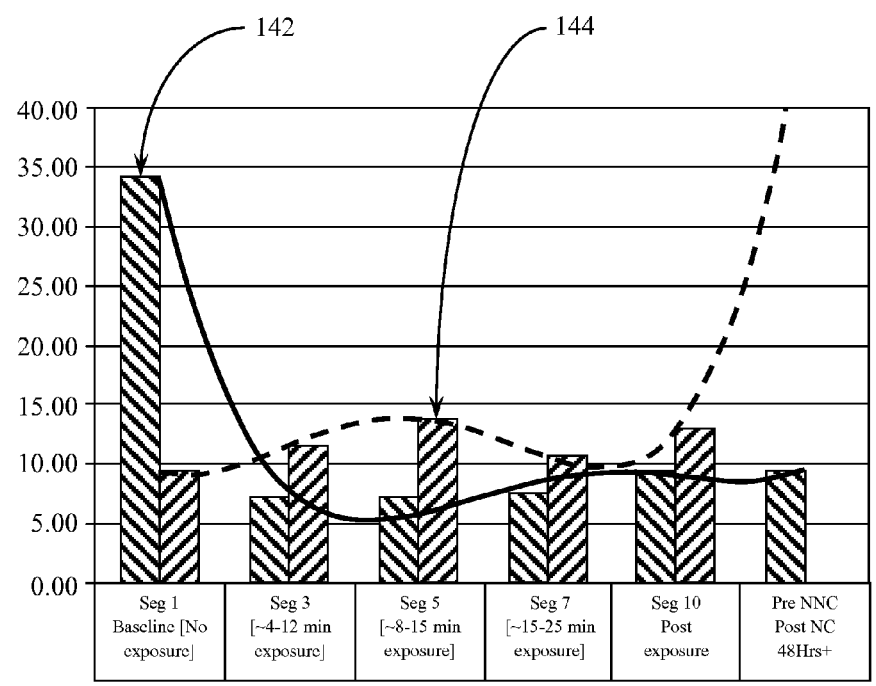
FIG. 14 is a bar graph illustrating full protocol and partial protocol β amplitude response.

FIG. 13 shows the full protocol 138 and partial protocol 140 SCP response. The SCP response of the full protocol showed rapid induction (greater blood flow to the frontal cortex), sustained effect, and rapid restoration of normal. FIG. 14 shows the full protocol 142 and partial protocol 144 β amplitude response. The β amplitude response of the full protocol showed rapid reduction of arousal and increased parasympathetic tone, sustained effect and maintenance. The median frequency of brain waves lowered from 17.3 Hz to 11.5 Hz with the full protocol of the present invention.

Figure 15:
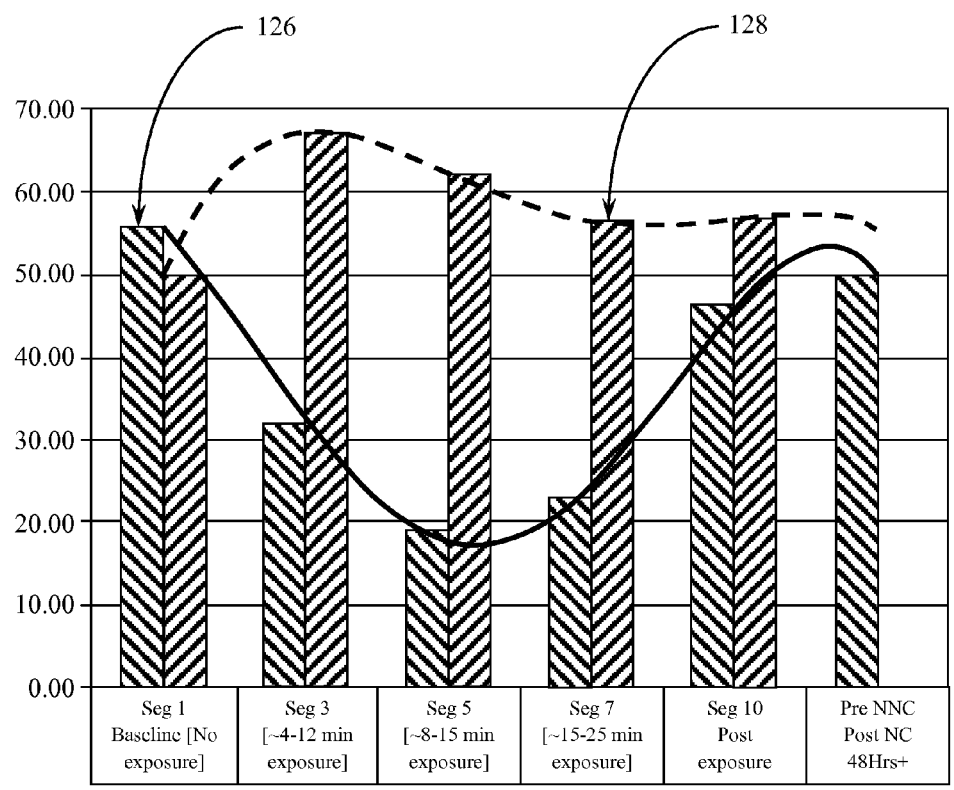
FIG. 15 is a bar graph illustrating full protocol and partial protocol δ amplitude response.
Figure 16:
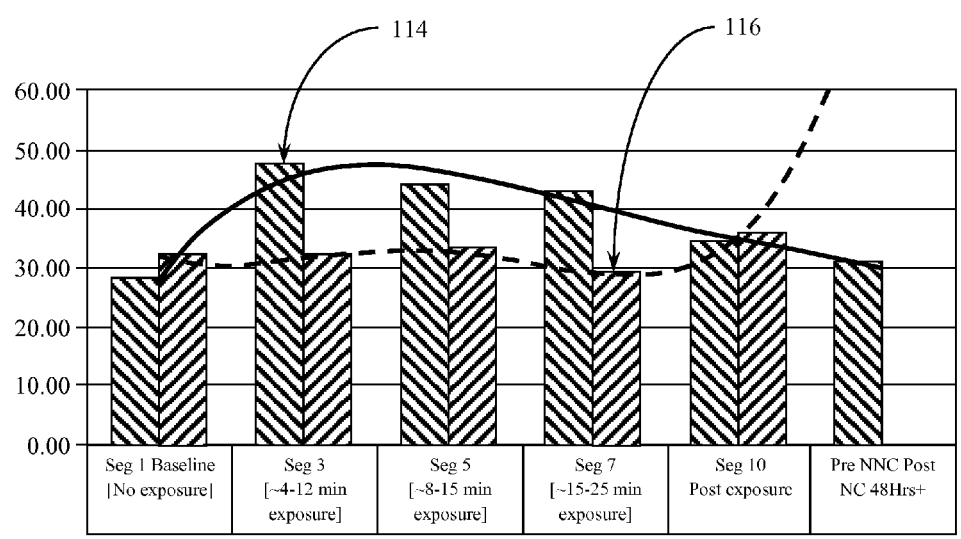
FIG. 16 is a bar graph illustrating full protocol and partial protocol % alpha over theta response.

Alpha theta crossover events increased from one event to nine events during the same time period with the full protocol of the present invention. The results indicate that there are statistically significant changes in the biophysiologic markers indicating a move toward a more parasympathetic (less aroused, hypnogogic) state with greater alpha brain wave dominance with the full protocol treatment as compared to the partial protocol. This dissociative sedative hypnotic entrainment was maintained throughout the application of the full protocol of the present invention and was evident across all categories of the biophysiological data collected. FIG. 15 shows the full protocol 126 and partial protocol 128 δ amplitude response. The δ amplitude response of the full protocol showed rapid hypnogogic induction, sustained effect, and rapid return to normal. FIG. 16 shows the full protocol 114 and partial protocol 116 % alpha over theta response. The % alpha over theta response of the full protocol showed rapid hypnogogic induction with sustained effect as well as rapid return to a normal state.

CONCLUSION

From the above it can be appreciated that the treatment modalities of the present invention have therapeutic applications to individuals who react with acute anxiety to dental and other medical procedures. Other benefits and applications of the present invention will be apparent to persons of ordinary skill in the art.

As used in the claims below, the term "neurotransmitter precursor/analog supplement" refers not only to supplements of natural neurotransmitters, but also to chemical supplements used by the body to synthesize a neurotransmitter, inhibit the reuptake of a neurotransmitter, or have an effect similar to that of a natural neurotransmitter.

Although the foregoing specific details describe various embodiments of the invention, persons reasonably skilled in the art will recognize that various changes may be made in the details of the apparatus of this invention without departing from the spirit and scope of the invention as defined in the appended claims. Therefore, it should be understood that, unless otherwise specified, this invention is not to be limited to the specific details shown and described herein.

I claim:

1. A therapeutic system for rapidly facilitating the balance and health maintenance of the autonomic nervous system (ANS), the therapeutic system for use in conjunction with a human patient, the therapeutic system comprising:
   (a) a therapeutic dosage of a neurotransmitter supplement for administering to the patient, wherein the neurotransmitter supplement is selected from gamma amino butyric acid (GABA), PhenylGABA, and combinations thereof;
   (b) at least one visual darkening eye cover reducing or eliminating the intensity of ambient light incident on the eyes of the patient;
   (c) a support platform, at least partially reclining, supporting the patient in a position that allows for relaxation of the support and mobility muscles of the patient;
   (d) a cranial electrotherapy stimulation (CES) device connected to the patient; and
   (e) a neuroacoustic entrainment system connected to the patient, the neuroacoustic entrainment system comprising at least one signal generator and stereo audio output devices, the neuroacoustic entrainment system generating signal tones of two different frequencies presented separately and simultaneously to each ear of the patient.

2. The therapeutic system of claim 1, wherein the neurotransmitter supplement is GABA.

3. The therapeutic system of claim 1, wherein the neurotransmitter supplement is PhenylGABA.

4. The therapeutic system of claim 1, wherein the neurotransmitter supplement is in a form suitable for administration orally.

5. The therapeutic system of claim 1, wherein the neurotransmitter supplement is in a form suitable for administration sublingually.

6. The therapeutic system of claim 1, wherein the neurotransmitter supplement is in a form suitable for administration transdermally.

7. A method for facilitating the balance and health maintenance of the autonomic nervous system (ANS), the method for use as a therapeutic protocol for a human patient, the method comprising the steps of:
   (a) administering a therapeutic dosage of a neurotransmitter supplement to the patient, wherein the neurotransmitter supplement is selected from gamma amino butyric acid (GABA), PhenylGABA, and combinations thereof;
   (b) positioning at least one visual darkening eye cover reducing or eliminating the intensity of incident ambient light over the eyes of the patient;
   (c) supporting the patient in a position that allows for relaxation of the support and mobility muscles of the patient;
   (d) administering cranial electrotherapy stimulation (CES) to the patient; and
   (e) administering a neuroacoustic entrainment program to the patient, the neuroacoustic software entrainment program generating signal tones of two different frequencies presented separately and simultaneously to each ear of the patient.

8. The method of claim 7, wherein the step of administering a neurotransmitter supplement comprises administering GABA.

9. The method of claim 7, wherein the step of administering a neurotransmitter supplement comprises administering PhenylGABA.

10. The method of claim 7 wherein the step of administering a neurotransmitter supplement comprises orally administering the neurotransmitter supplement.

11. The method of claim 7 wherein the step of administering a neurotransmitter supplement comprises sublingually administering the neurotransmitter supplement.

12. The method of claim 7 wherein the step of administering a neurotransmitter supplement comprises transdermally administering the neurotransmitter supplement.

13. The method of claim 7 further comprising the step of determining the need for administering a second therapeutic dosage of a neurotransmitter supplement and, if so, administering a second therapeutic dosage of a neurotransmitter supplement.

* * * * *